United States Patent [19]

Surgenor

[11] Patent Number: 5,017,338

[45] Date of Patent: May 21, 1991

[54] PLATELET CONCENTRATES

[75] Inventor: Douglas M. Surgenor, Carlisle, Mass.

[73] Assignee: The Center for Blood Research, Inc., Boston, Mass.

[21] Appl. No.: 850,759

[22] Filed: Apr. 11, 1986

[51] Int. Cl.$^5$ .............................................. A61B 19/00
[52] U.S. Cl. ........................................ 422/41; 422/44;
422/102; 422/104; 436/176; 435/2; 435/310;
604/408; 128/767; 128/DIG. 24; 73/864.62
[58] Field of Search .................... 422/41, 58, 44, 102,
422/48, 104; 436/165, 176; 210/232; 128/DIG.
24, 767; 604/408; 73/864.62; 435/2, 310, 809

[56] References Cited

U.S. PATENT DOCUMENTS 4,132,594 1/1979 Bank et al. ...................... 422/41 X
4,337,769 7/1982 Olson ............................. 604/408 X

FOREIGN PATENT DOCUMENTS 0102302 3/1984 European Pat. Off. ............ 604/408
0036481 3/1980 Japan ..................................... 435/2

Primary Examiner—David L. Lacey
Assistant Examiner—L. M. Kummert
Attorney, Agent, or Firm—Wolf, Greenfield & Sacks

[57] ABSTRACT

Method for storing, preserving and transporting concentrates of human platelets under blood bank conditions prior to transfusion by compressing plastic walled platelet bags with the use of a grid to permit gas circulation to the bag with the bag positioned for storage in a desired position. A grid aids in storing and preserving platelets and has a rigid body with a substantial open area configured to substantially compress a side of a plastic walled platelet bag to form a substantially uniform layer of fluid in the bag to maximize gas transfer capacity and permit long storage life at atmospheric conditions without the need for conventional agitation of the bag.

9 Claims, 4 Drawing Sheets

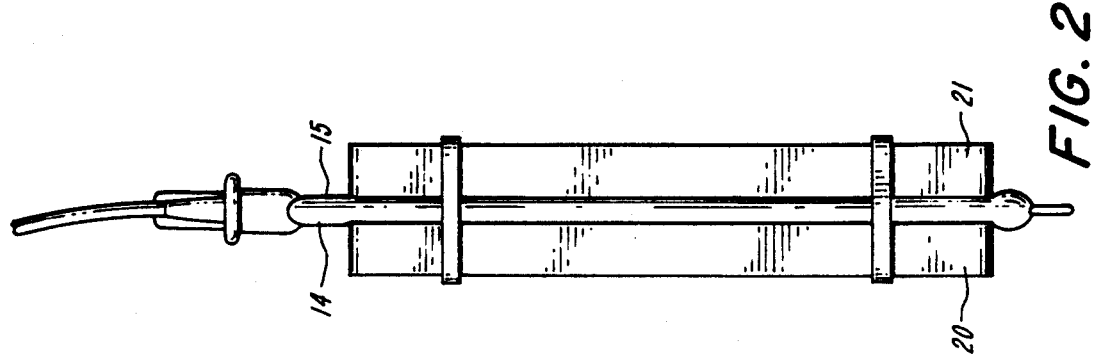
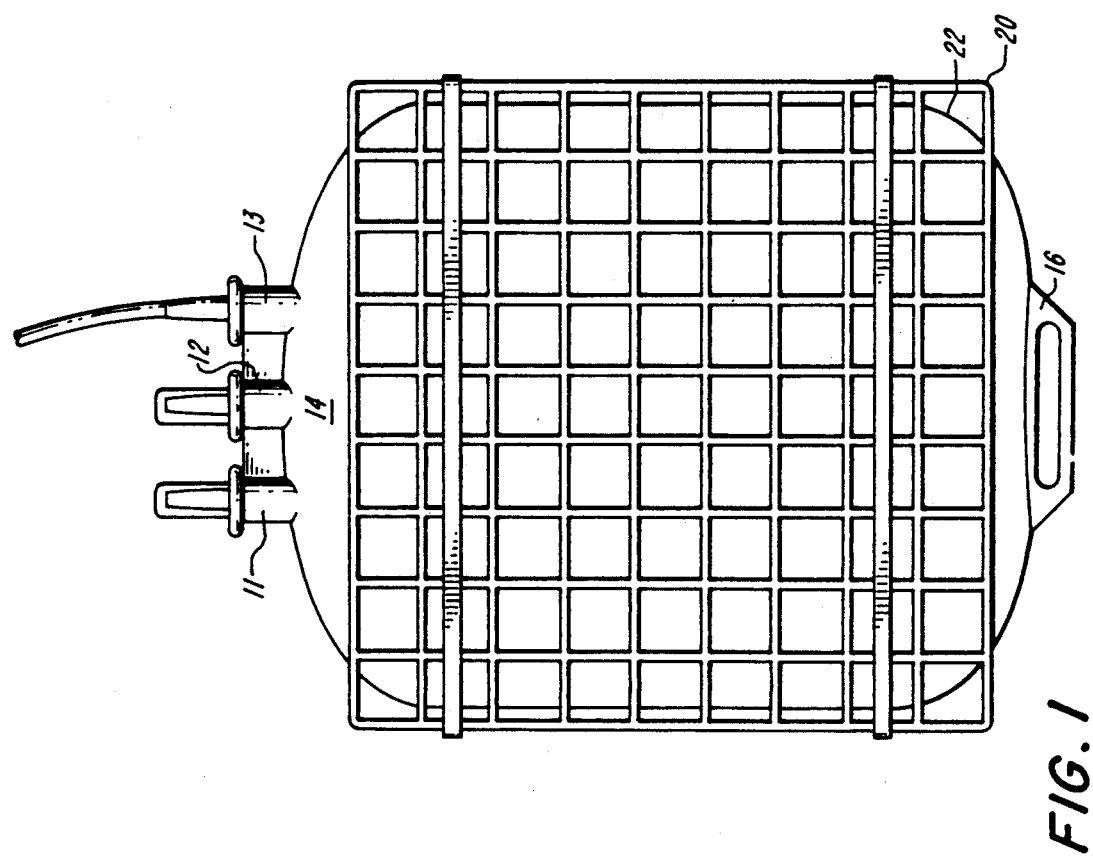

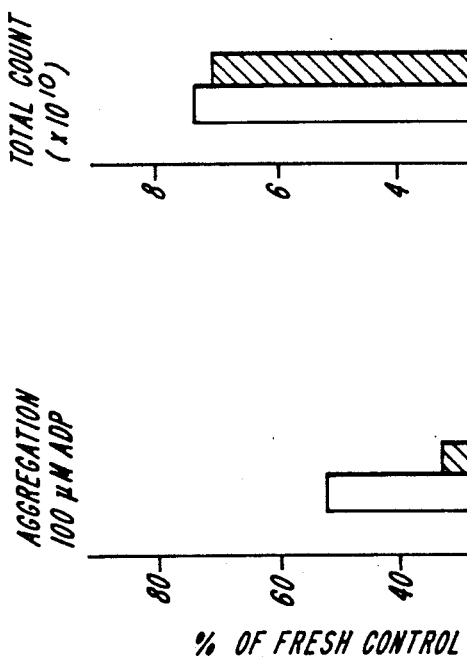
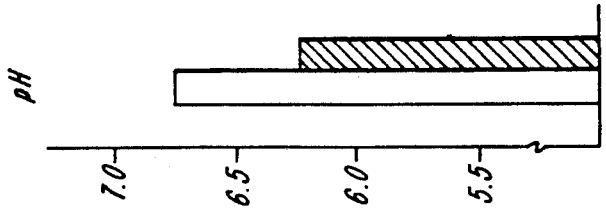
FIG. 3A  FIG. 3B  FIG. 3C  FIG. 3D  FIG. 3C

FIG. 4D
FIG. 4E
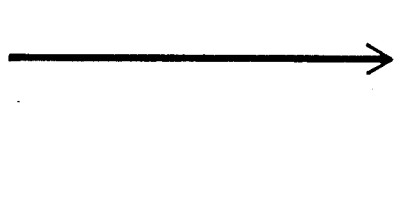
FIG. 4C
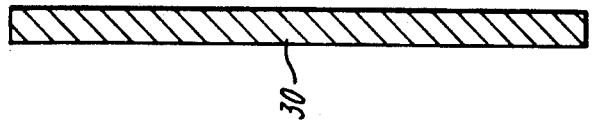
FIG. 4A   FIG. 4B

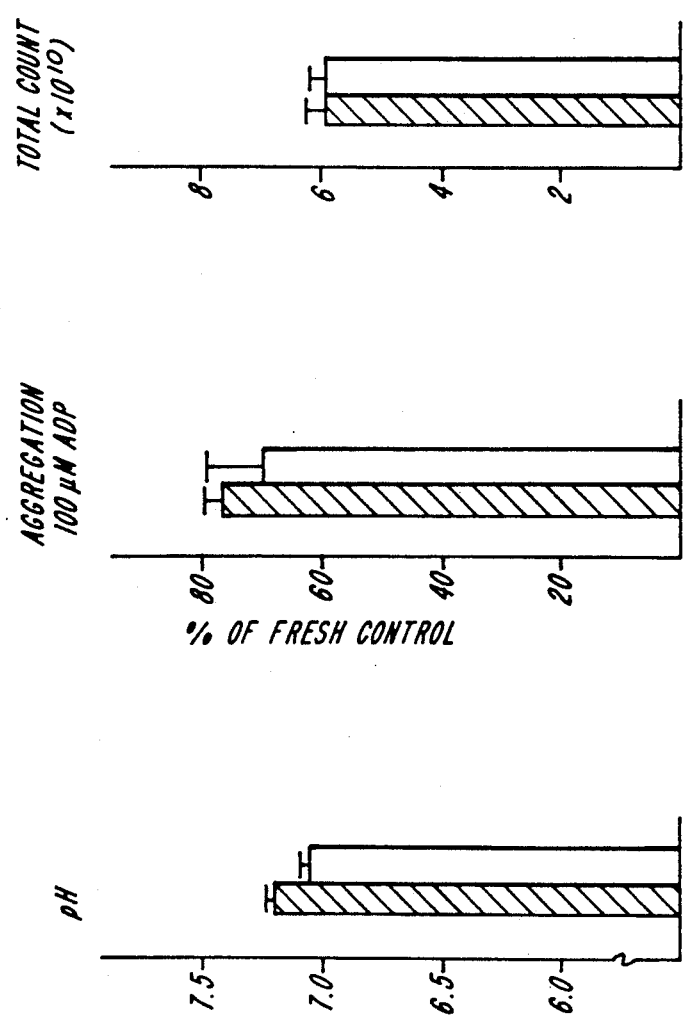

PLATELET CONCENTRATES

This invention was made with government support under Contract No. NAS 9-1722 awarded by N.A.S.A The government has certain rights in this invention.

BACKGROUND OF THE INVENTION

Human platelet transfusion is widely employed in the management of patients with bleeding problems. As routinely conducted in regional blood banks, the method of platelet preservation, transportation and utilization involves a series of general steps which include collecting whole blood from the donor into a blood bag containing anti-coagulant solution. In a second step platelet-rich plasma (PRP) in a volume of about 250 ml is then separated from other blood cells by differential centrifugation. The platelets are concentrated in the PRP by centrifugation. Packed platelets are then separated in 50-60 ml of plasma. The packed platelets are routinely then resuspended by allowing the cells to rest in a blood bag at room temperature. The platelet concentrates then obtained are used for transfusion. For neonates up to there months old or newborns and infants who are in need of platelet concentrations but cannot tolerate 50-60 ml volume of plasma, plaltelets in the concentration normally obtained are further concentrated by centrifugation with excess plasma removed and the platelets then rested and agitated again. The step to further concentrate can take at least two hours to produce approximately 10 ml of highly concentrated platelets.

The platelets can be transported in many ways but generally are transported in plastic blood bags containing platelet concentrates placed in a box for shipping. Agitation is required in the current method of platelet preservation but may not be applied during transportation for short periods of time. When agitation is not used even for short periods, viability may be decreased particularly if transportation is over long distances and takes some time.

Agitation, which keeps platelets in suspension throughout the perservation period, has in the past been used for storage under earth gravity in order to facilitate gas transport to a surrounding atomosphere. Platelets are metabolically active cells which require oxygen to maintain their viability; at the same time, carbon dioxide must be removed from the plasma or fluid medium surrounding the platelets, otherwise the pH of the suspension can fall and injure the platelets. The oxygen and carbon dioxide must diffuse through the plastic wall of the containers. Failure to agitate platelets during storage can lead to a more rapid fall in pH and a reduction in viability. A fall in pH is always associated with poor platelet perservation with a fall below pH 6.0 being destructive of the platlelets or their function after transfusion into an individual. Diffusion of oxygen and carbon dioxide can be facilitated by agitation of the plastic bag. However, agitation-produced damage to platelets can be demonstrated by a variety of tests which assess platelet function. Generally speaking, the more vigorous the agitation, the more platelet destruction. Force which results in increased platelet-platelet or platelet-surface interactions is deliterious to platelets.

SUMMARY OF THE INVENTION

It is an object of this invention to provide a means and method for storing and preserving platelets suspended in a fluid which means and method can be easily carried out without great expense and is suitable for wide scale use by relatively unskilled persons.

It is another object of this invention to provide a means and method in accordance with the proceding object which utilizes a grid body to compress a platelet bag to form a thin layer of platelets carried in fluid to maximize contact area of the fluid wiht a surrounding atmosphere.

It is another object of this invention to provide a means and method in accordance with the preceding objects which provides for long platelet life during storage and handling without the need for mechanical agitation and with inexpensive means and methods using conventional plastic storage bags for the platelets.

According to the invention platelets are stored and preserved by being suspended in a fluid such as plasma and are carried in a thin wall, non-rigid, plastic bag having first and second yieldable side walls. The sides are compressed to form a substantially thin, preferably uniform, layer of the fluid within the bag to maximize fluid contact with the sides of the bag. The bag is compressed with the use of a grid means which permits gas circulation preferably to both sides of the bag. The bag is positioned in a desired position for storage. Preferably the bag is positioned upright and more preferably substantially vertically when the bag is to be left in the atmosphere under standard atmospheric conditions. In some case where enhanced gas flow is provided around the bag, the position of the bag may change. Preferably the layer is a uniform layer having a thickness of about 0.3 centimeters although somewhat higher and lower thicknesses below ½ inch can be used and most preferably below ¼ inch can be used to enhance storing properties.

A grid means is provided for aiding and storing and preserving platelets suspended in fluid and carried in a thin wall, non-rigid plastic bag having first and second opposed side walls defining surfaces of a predetermined area for gas transfer. The grid means comprises a first rigid body with substantial opened area and configured to substantially compress a side of the bag to form a thin and preferably substantially uniform layer of fluid in the bag. Most preferably a second rigid body is used opposed to the first rigid body with the bag compressed between the two in a sandwich-like arrangement to form a thin uniform layer within the bag and thus maximized gas transfer through the walls of the bag.

It is a feature of this invention that the platelet concentrate is preferably formed into a minimum liquid film thickness with maximum surface area directly contacting the side walls of the bag to facilitate gas transport through the walls and thus enabling the platelets to be preserved at standard atmospheric conditions of for example 20° C. and 14.7 PSI without the need for agitation. Storage can be carried out at ambient temperatures of from for example 35° to 95° F. The grid means can be inexpensive devices clamped together by rubber bands or other conventional clamps. Relatively untrained personnel can be easily taught to apply the compression means. Conventional plastic bags and conventional platelet handling techniques for the bags can be used. Thus, the grid means can be applied to conventional platelets bags as now used in blood banks.

BRIEF DESCRIPTION OF THE DRAWINGS

The above and other objects, advantages and features of the present invention will be better understood from the following specification when read in conjunction with the accompanying drawings in which:

FIG. 1 is a front view of a platelet bag and grid means construction in accordance with a preferred embodiment of this invention;

FIG. 2 is a side view thereof;

FIG. 3 is a chart illustrating a comparison of compressed vs. non-compressed platelet storage;

FIGS. 4A-E are diagrammatic showings of platelet storage positions; and

FIG. 5 is a further chart illustrating a further comprasion of compressed vs. non-compressed platelets

BRIEF DESCRIPTION OF PREFERRED EMBODIMENTS

Human or animal platelets are preserved for transfusion by physically configuring a sterile liquid platelet suspension within a pliable, non-rigid plastic container or bag so as to obtain a preferably uniform and minimum thickness of liquid suspension in contact with the entire or maximum inner surface of the plastic bag. This optimizes the desired conditions, that is, maximum surface area, minimum liquid thickness and minimum length of path through liquid for gas transfer to allow the passive diffusion of oxygen from the external environment outside of the bag to the respiring platelets within the bag for passive diffusion of carbon dioxide from the platelets to the external environment.

The bags can be conventional plastic bags used and filled with platelets in accordance with conventional procedures as above described. Thus the plastic of the bags can be any thin film plastic bag compositions including conventional compositions such as FDA approved blood bags formed of polyolefin and polyvinyl chloride-trioctoltrimalitate (PVC-TOTM) or polyvinyl chloride -di-2-ethylhexylphalate PVC-DEHP bags. The plastic films of the bag side walls are preferably in thickness of 0.015 inch or less in order to maximize gas transfer. The better the gas transfer properties of the plastic without harming the platelets suspended within the fluid or plasma in the bags, the more desirable the configuration is for use in connection with the present invention. Preferably the oxygen transmission rate of the bag walls is from about 20 to about 50 ml per 100 square inch per 24 hours at standard room temperature of 20° C. and standard atmospheric pressure. The routine blood bank standards can be used such as a minimum total number of platelets in a stored concentrate of greater than $5 \times 10^{10}$ cells in a volume of 50-60 ml or for infants, concentrations of from $5 \times 10^{10}$ platelets per 10 ml of plasma. The bags are only partially filled and have a capacity to hold 300 ml. The bags have first and second flat sides as shown in FIGS. 1 and 2. The blood bag side walls have approximate dimensions of $13 \times 14.5$ cm with outer surface areas of 188.5 cm$^2$. As best shown in FIG. 1 a bag 10 has conventional fill and outlet ports 11, 12 and 13 with side walls 14 and 15. The bag is substantially flat, non-rigid and thin walled with a holding or hanging nib 16 at the bottom.

The grid means useful in the present invention can be any opened area rigid grid that can act to rigidify the walls of the plastic bag, Thus, the grid means can be rigid metal, plastic grids, meshes or screens. In the preferred embodiment shown in FIG. 1 and FIG. 2 a pair of plastic grids 20 and 21 each identical to the other are shown. The plastic grids may have dimensions such that the body of each grid, that is, the solid strut members 22 take up a total area of about 16% of the overall total area of the grids with a ratio of clear or airhole to solid area being 5.25. Preferably a minimal ratio of solid to air is used while providing sufficient strength to rigidify the side walls of the bag while compressing the fluid to a minimized thin layer. Preferably the ratio of clear airholes and solid area is 5.25 although a higher ratio could be used as long as the grid is rigid enough to compress the platelet concentrate in the blood bag to a minimal thickness and preferably a uniform thickness. Preferably each grid is approximately the size of each bag, i.e., for a $13 \times 14.5$ cm size side wall the grids used may be about $14 \times 15$ cm. However, in some cases larger compressing grids may be used to simultaneously compress two or more bags. The thickness of the grid means can vary and is preferably only thick enough to provide strength necessary for rigidity of the grid to flatten the side wall.

According to routine blood bank standards, the minimal total number of platelets in the stored concentrate should be greater than $5 \times 10^{10}$ cells in a volume of 50-60 ml of plasma. Preferably at least 5 days of storage time is obtained by the use of the means and method of the present invention. Compression works well at concentrations of $1.0-1.4 \times 10^9$ platelets per ml.

Note that the thin preferably uniform liquid film after compression is preferably about 0.3 centimeters or less than ⅛ inch and most preferably below ¼ inch as compared to a thickness of plasma platelet concentrate in a blood bag when held upright without compression of about ½ inch. Platelets deteriorate rapidly during storage in the latter condition without agitation.

The grid means which can be a honeycomb plastic as shown in FIGS. 1 and 2 can be held in place and compress the bag in a sandwich, as shown in FIG. 2, by the use of rubber bands. Minimal pressure is required. Preferably the pressure applied is sufficient to rigidify the bag with the preferred thin uniform layer of fluid within the thin plastic walls as best shown in FIG. 2. Higher pressures can be used although they are unnecessary. Clamps, screws, pins or other compression means can be used in place of the rubber bands. The rubber band in simple plastic grid honeycomb construction provide for an inexpensive easily applied compression grid means for use in carrying out the invention by unskilled labor at minimized cost and expense.

Platelet function tests can be used to assess the efficiency of platelet storage. Two in vitro measurements are suggested by the FDA regulations which are pH and total platelet count for routine quality control of blood bank stored platelet units. The acceptable level of pH is no less than 6.0 and total platelet counts must be greater than $5.5 \times 10^{10}$ platelets in a volume of 50-60 ml of plasma after preservation. A loss of platelet viability after storage is measured by other platelet function tests in vitro as well as the two FDA specifications in the discussion below. Partial pressure of oxygen and carbon dioxide were measured simultaneously in all the following experiments. The efficiency of platelet storage is measured by recovery and survival of transfused stored platelets in vivo. Viable stored platelets survive and recirculate whereas defective platelets caused by unsatisfactory storage condition are removed from circulation after transfusion.

In FIG. 3, it is shown that compression alone without agitation is superior for platelet storage compared to non-compressed, non-agitated platelet units. A loss of platelet viability is indicated by the decrease of platelet response to hypertonic stress tests (PRHS), the reduction of aggregation response to adenosin diphosphate (ADP) and the increase of mean platelet volume (MPV). In this experiment, both compressed (n=4) and non-compressed (n=3) was stored vertically for 6 days at 22° C. without agitation. In each case the platelet bags stored were 15 mil sidewall polyolefin or PVC-TOTM having sidewall dimensions of about 14.5 cm × 12.0 cm. The grid means for compression had an air hole to solid ratio of 5.25 and was formed of plastic as illustrated in FIGS. 1 and 2. A 60 ml plasma volume is used with a platelet concentration of $1.25 \times 10^9$ cell ml.

The success of the compressed bags of this invention is believed due to improvement in the movement of respiratory gases particularly of carbon dioxide as is suggested by experiments in which platelet sandwiches are stored within a closed chamber which is supplied with a flow of air. Survival is found to be very sensitive to air flow rates, being poorest at low flow rates and best at high flow rates. Survival in vertical sandwiches in an open laboratory are comparable to survival in the highest air flow rates (90 cc per minute or greater in a closed system). All experiments are conducted in an open laboratory under standard environmental conditions of 20° C. and standard atmospheric pressure. The orientation of the platelet sandwich with respect to gravity during the preservation period is important. Superior survival of platelets is obtained when the sandwich is kept in a vertical position in comparison to the horizontal condition as shown in Table 1 below. The pH of horizontally stored platelets without agitation and without increased gas flow can fall below the acceptable level of ph 6.0. While the vertical or upright position is preferred, in some cases a horizontal position can be used as when gas flow rates are increased.

TABLE 1

STORAGE OF COMPRESSED PLATELET UNITS IN THE VERTICAL AND HORIZONTAL POSITION

| Orientation | Agitation | No. of Expt. | pH (mean ± SD) | Total Plt. Counts mean ± SD; $10^{10}$ |
|---|---|---|---|---|
| Horizontal | no | 4 | 5.83 ± 0.12 | 9.14 ± 0.48 |
| Vertical | no | 4 | 6.99 ± 0.04 | 9.99 ± −029 |

FIG. 4 shows graphically what is happening within a compressed platelet suspension during long storage without agitation. In the vertical position of bags A and B, there is some sedimentation of the suspended platelets 30, but because the platelets have a low specific gravity, sedimentation is slow and occurs primarily in the direction of other platelets arrow C, rather than toward a plastic surface; this may be a favorable factor. By contrast, storage of the sandwich in the horizontal position of bags D and E produces a quite different result. Given the uniformly thin layer of suspension, the platelets have only a short distance to sediment before they hit the "bottom" and interact with a plastic surface which may be an unfavorable condition for storage.

When the standard blood bank platelet bags described above are tested at compression storage (without agitation) for 7 days at room temperature in the vertical position both pH and total platelet counts are within the acceptable range (Table 2). All 12 units of platelets stored by the compression method had pH above 6.0 (11 units with pH above 6.8; 1 unit at 6.4). Only 1 of the 12 units (8.3%) had total platelet counts ($4.3 \times 10^{10}$) below the acceptable level. The control units were stored under the standard blood condition with constant agitation. There were no significant differences of pH and total platelet count between platelets stored by these two methods.

TABLE 2

QUALITY CONTROL DATA OF PLATELET CONCENTRATES STORED BY THE COMPRESSION AND AGITATION METHODS*

| Orientation | Agitation | No. of Expt. | pH (mean ± SD) | Total Plt. Counts mean ± SD; $10^{10}$ |
|---|---|---|---|---|
| Compression | no | 12 | 6.92 ± 0.19 | 8.0 ± 1.9 |
| Standard Blood Bank | yes | 11 | 7.02 ± 0.07 | 9.0 ± 1.3 |
| t-test** | | | NS | NS |

*Platelet concentrates (PC) were prepared from citrate-phosphate-dextrose anticoagulated whole blood by the standard blood bank procedure. Resuspended platelet concentrates were distributed in polyolefin or polyvinyl chloride plasticized with trioctyltrimellitate (TOTM) bags. Both bags are used in blood banks for 7 days at room temperature by compression in the vertical position or by the standard blood bank method with constant agitation.
**The differences of pH and total platelet counts between platelets stored by the two methods are not statistically significant (NS).

Platelets stored by compression for 7 days in the vertical position showed similar post-transfusion yield and survival to those stored by the agitation method. There are no statistically significant differences between these two methods.

TABLE 3

IN VIVO SURVIVAL OF PLATELETS STORED FOR 7 DAYS AT 22° C. Compression vs Agitation

| Storage Condition | No. of Expt. | % Yield[1] (mean ± SD) | T ½- days[2] (mean ± SD) | Survival days[3] (mean ± SD) |
|---|---|---|---|---|
| Compression | 5 | 39.3 ± 7.5 | 3.7 ± 0.3 | 7.5 ± 0.4 |
| Agitation | 2 | 40.0 ± 1.4 | 4.1 ± 0.3 | 8.3 + 0.6 |

[1]Yield - Maximal post-transfusion recovery
[2]T ½ - Half-life of surviving transfused platelets
[3]Survival - Life span of transfused platelets The results of other laboratory measurements from an experiment comparing platelet storage by compression and agitation are summarized in FIG. 5. Both control (agitated) and test (compressed) units showed a slight loss of platelet viability evidenced by the reduction of aggregation response to ADP, the decrease of PRHS and the increase of MPV. The differences between agitated and compressed platelets were not significantly different with respect to pH, mean platelet volume, aggregation response to ADP and total platelet count. However, the difference in platelet response to hypotonic stress though small was statistically significant at the $p < 0.05$ level.

In summary, the present invention provides a standard, easy and economic method for storage, preservation and transportation of platelet concentrates. It reduces the deleterious effect of added physical force upon platelet-platelet and platelet-container wall interaction which can occur during storage with agitation. For transfusion of neonates and infants, it can shorten the time required for preparing highly concentrated platelets in a small volume of plasma (10 ml) from at least two hours to approximately 10 minutes. This is possible since vertical storage allows the platelets to settle and separate from the plasma over storage time so that one can merely remove excess plasma from the top of the bag and use the lower platelet-rich portion without the need for centrifugation.

It should be understood that although specific embodiments have been shown and described, many variations are possible. The size of the platelet bags, the specific materials and the volumes contained can vary greatly as discussed. In all cases, the formation of a thin layer by compression of the container bag against the fluid, is carried out to maximize surface transfer area allowing good gas diffusion.

What is claimed is:

1. A method of storing and preserving platelets suspended in a fluid and carried in a thin wall, non-rigid, plastic bag having first and second yieldable side walls,
said method comprising compressing said side walls to form a substantially thin layers of said fluid within said bag,
said compressing being carried out by rigid grid means which permit gas circulation to at least one of said side walls,
and positioning said bag for storage in a desired position.

2. A method in accordance with the method of claim 1 wherein said thin layer of fluid is positioned in a substantially vertical position.

3. A method in accordance with the method of claim 2 wherein said bag contains a minimal total number of platelets stored in the bag at a concentration of $5 \times 10^{10}$ cells in a volume of 50-60 ml of plasma.

4. A method in accordance with claim 1 wherein said thin layer of fluid has a thickness of about 0.3 cm.

5. A method in accordance with claim 4 wherein said platelets are stored and preserved for about 7 days at room temperature without agitation.

6. A method in accordance with claim 4 wherein said bag is formed of a thin walled plastic having a wall thickness of 0.020 inch or less.

7. A method in accordance with claim 4 wherein said bag walls have an oxygen transmission rate of from about 20 to about 50 ml per 100 square inch per 24 hours when stored at room temperature and pressure.

8. A method in accordance with claim 7 wherein said grid means comprises grids having solid mass areas and opened areas with the solid mass areas of said grids occupying about 16% of the total grid solid mass areas and opened areas and the ratio of opened areas to solid mass areas being about 5.25.

9. A method in accordance with claim 1 wherein said thin layer of fluid is uniform and platelets can be stored and preserved for at least 5 days at room temperature without agitation.

* * * * *